US010925757B2

(12) United States Patent
Weidenhamer et al.

(10) Patent No.: US 10,925,757 B2
(45) Date of Patent: Feb. 23, 2021

(54) TISSUE-COATED ARTICLES

(71) Applicant: Medtronic Vascular, Inc., Santa Rosa, CA (US)

(72) Inventors: Nathan Weidenhamer, Minneapolis, MN (US); Jeffrey Vogel, Brooklyn Park, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 156 days.

(21) Appl. No.: 15/927,116

(22) Filed: Mar. 21, 2018

(65) Prior Publication Data

US 2019/0290461 A1    Sep. 26, 2019

(51) Int. Cl.
| | | |
|---|---|---|
| *A61F 2/91* | (2013.01) | |
| *A61L 31/08* | (2006.01) | |
| *A61L 31/14* | (2006.01) | |
| *A61L 31/16* | (2006.01) | |
| *A61L 31/10* | (2006.01) | |

(52) U.S. Cl.
CPC ............... *A61F 2/91* (2013.01); *A61L 31/10* (2013.01); *A61L 31/148* (2013.01); *A61L 31/16* (2013.01); *A61F 2310/00982* (2013.01); *A61L 31/08* (2013.01); *A61L 2300/606* (2013.01); *A61L 2420/02* (2013.01); *A61L 2420/08* (2013.01)

(58) Field of Classification Search
CPC ........................................................ A61F 2/91
See application file for complete search history.

(56) References Cited

U.S. PATENT DOCUMENTS

| | | | | |
|---|---|---|---|---|
| 6,096,073 | A | * | 8/2000 | Webster ................ A61F 2/91 623/1.16 |
| 6,475,232 | B1 | * | 11/2002 | Babbs .................. A61F 2/07 623/1.13 |
| 6,752,826 | B2 | | 6/2004 | Holloway et al. |
| 7,244,444 | B2 | | 7/2007 | Bates |
| 7,686,842 | B2 | | 3/2010 | Pavcnik et al. |
| 7,914,567 | B2 | | 3/2011 | Pavcnik et al. |
| 2003/0009213 | A1 | | 1/2003 | Yang |
| 2005/0013870 | A1 | | 1/2005 | Freyman et al. |
| 2007/0162103 | A1 | * | 7/2007 | Case .................... A61F 2/2412 623/1.13 |

(Continued)

FOREIGN PATENT DOCUMENTS

| | | |
|---|---|---|
| EP | 1923025 A2 | 5/2008 |
| WO | 20100101780 A2 | 9/2010 |
| WO | 20170176919 A1 | 10/2017 |

OTHER PUBLICATIONS

EP19163431.0 Extended European Search Report, dated Aug. 27, 2019, 10pgs.

(Continued)

*Primary Examiner* — Leslie Lopez
(74) *Attorney, Agent, or Firm* — Shumaker & Sieffert, P.A.

(57) ABSTRACT

Example articles coated with tissue layers and techniques for forming articles with tissue layers. An example article may include a tubular frame extending along a longitudinal axis. The tubular frame includes a plurality of struts joined at apices to define a plurality of cells including a group of struts. The example article includes a tissue layer coating each strut and extending across each cell. The tissue layer defines a plurality of defects, each cell including a respective defect.

16 Claims, 4 Drawing Sheets

(56) References Cited

U.S. PATENT DOCUMENTS

2007/0178221 A1* 8/2007 Sims .................. A61F 2/915
427/2.21
2008/0033522 A1 2/2008 Grewe et al.
2009/0238853 A1 9/2009 Liu et al.
2010/0191323 A1 7/2010 Cox
2011/0264190 A1 10/2011 McClain et al.
2014/0330377 A1 11/2014 Niklason et al.

OTHER PUBLICATIONS

Liping Zhao et al., "Engineered Tissue-Stent Biocomposites as Tracheal Replacements" Tissue Engineering Part A, vol. 22, No. 17-18, Sep. 1, 2016.
Dr. Chinn, "Prohealing Coatings: A Revolution in Medical Device Surface Modification," Nov. 5, 2007, accessed on Sep. 13, 2017 from https://www.mdtmag.com/article/2007/11/prohealing-coatings-revolution-medical-device-surface-modification, 8 pp.
Wang, et al., "Fabrication of tissue-engineered vascular grafts with stem cells and stem cell-derived vascular cells," Expert Opin. Biol. Ther., 2016, published online Nov. 11, 2015, 23 pp.
Nair, et al., "Biodegradable polymers as biomaterials," ScienceDirect, Prog. Polym. Sci, Aug.-Sep. 2007, vol. 32, Issues 8-9, pp. 762-798.

* cited by examiner

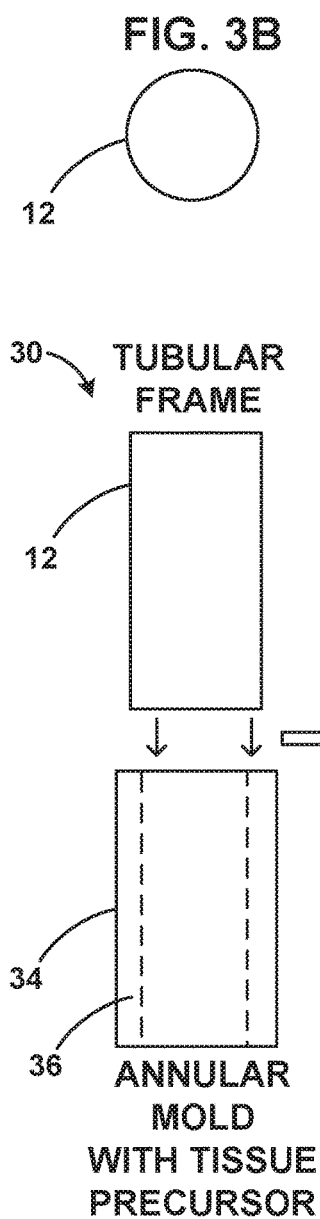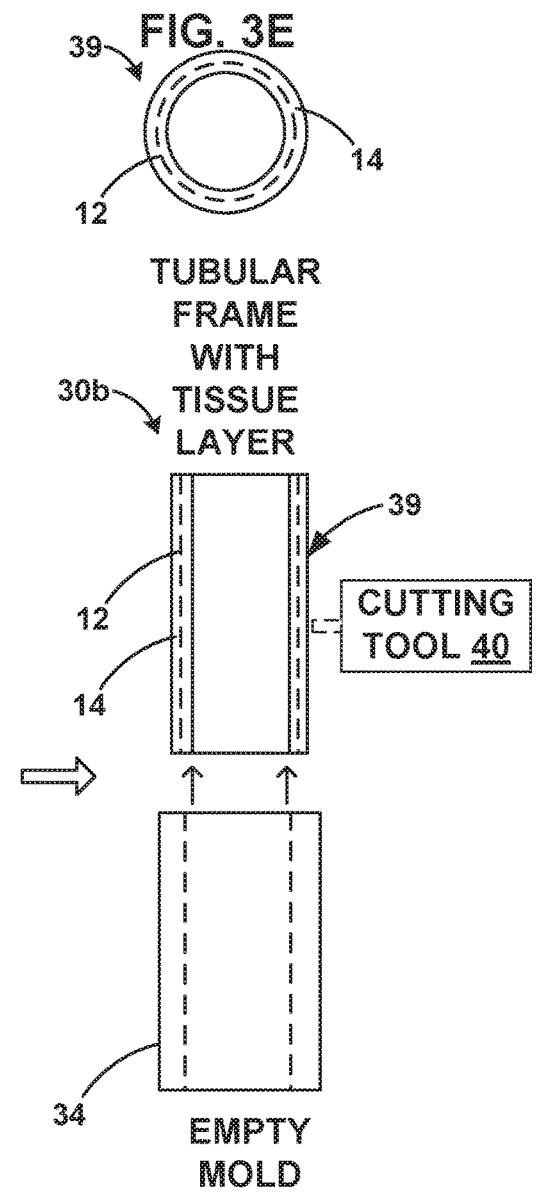

TISSUE-COATED ARTICLES

TECHNICAL FIELD

The present disclosure relates to, in some examples, articles coated with biological tissue, in particular, medical articles coated with tissue, and techniques for coating articles with tissue.

BACKGROUND

A functional endothelium may prevent thrombosis and maintain homeostasis of blood vessels. Disruption of the endothelium or endothelial dysfunction may lead to initiation of the coagulation cascade and thrombosis. Medical articles, for example, stents, may be introduced into the vasculature to keep vessels open. One or more surfaces of such medical articles, for example, bare metal surfaces, introduced into vasculature or other vessels may contact and apply pressure on the endothelium or other tissue.

SUMMARY OF THE DISCLOSURE

Medical articles coated with tissue may relatively rapidly reendothelialize after introduction into vessels and provide a relatively more biocompatible surface, potentially reducing or preventing rethrombosis or other effects or conditions.

In some examples, the disclosure describes an example article including a tubular frame extending along a longitudinal axis. The tubular frame includes a plurality of struts joined at apices to define a plurality of cells. Each cell of the plurality of cells includes a group of struts of the plurality of struts. The example article includes a tissue layer coating each strut of the plurality of struts and extending across each cell of the plurality of cells. The tissue layer defines a plurality of defects. Each cell of the plurality of cells includes a respective defect of the plurality of defects.

In some examples, the disclosure describes an example technique including applying a biomaterial scaffold to a tubular frame. The tubular frame includes a plurality of struts joined at apices to define a plurality of cells. The example technique includes culturing the biomaterial scaffold on the tubular frame in a culture medium to form a tissue layer. The tissue layer coats each strut of the plurality of struts and extends across each cell of the plurality of cells. The example technique includes perforating the tissue layer to form a plurality of defects such that each cell of the plurality of cells includes at least one defect of the plurality of defects.

Clause 1: An article comprising: a tubular frame extending along a longitudinal axis, the tubular frame comprising: a plurality of struts joined at apices to define a plurality of cells, each cell of the plurality of cells comprising a group of struts of the plurality of struts; and a tissue layer coating each strut of the plurality of struts and extending across each cell of the plurality of cells, the tissue layer defining a plurality of defects, each cell of the plurality of cells including a respective defect of the plurality of defects.

Clause 2: The article of clause 1, wherein at least one defect of the plurality of defects includes at least one slit or at least one opening.

Clause 3: The article of clause 2, wherein the at least one slit or at least one opening is configured to expand in response to an expansion of the tubular frame to define a respective window.

Clause 4: The article of any of clauses 1 to 3, wherein at least one defect of the plurality of defects defines a respective window in each cell of the plurality of cells.

Clause 5: The article of clause 4, wherein each respective window defines a polygonal edge.

Clause 6: The article of clause 4, wherein each respective window defines a curved edge.

Clause 7: The article of any of clauses 1 to 6, wherein the plurality of cells is configured to: collapse to compress the tubular frame into a compressed state, wherein each defect of the plurality of defects is substantially closed in the compressed state; and expand to expand the tubular frame into an expanded state, wherein each defect of the plurality of defects is substantially open in the expanded state.

Clause 8: The article of any of clauses 1 to 7, wherein the tissue layer is substantially free of live cells.

Clause 9: The article of any of clauses 1 to 9, wherein the tissue layer comprises extracellular matrix.

Clause 10: A method comprising: applying a biomaterial scaffold to a tubular frame comprising a plurality of struts joined at apices to define a plurality of cells; culturing the biomaterial scaffold on the tubular frame in a culture medium to form a tissue layer coating each strut of the plurality of struts and extending across each cell of the plurality of cells; and perforating the tissue layer to form a plurality of defects such that each cell of the plurality of cells includes at least one defect of the plurality of defects.

Clause 11: The method of clause 10, wherein the biomaterial scaffold comprises one or more of fibrin, collagen, alginate, polyglycolic acid, or polylactic acid.

Clause 12: The method of clause 10 or clause 11, further comprising, before the culturing, seeding the biomaterial scaffold with a plurality of biological cells, wherein the biological cells are configured to transform the biomaterial scaffold to tissue in response to the culturing to form the tissue layer.

Clause 13: The method of clause 12, wherein the biological cells comprise one or more of fibroblasts, smooth muscle cells, endothelial cells, epithelial cells, or cells derived from stem cells.

Clause 14: The method of clause 12 or clause 13, further comprising, after the culturing, substantially decellularizing the tissue layer.

Clause 15: The method of any of clauses 10 to 14, wherein the applying the biomaterial scaffold comprises one or more of spraying, coating, brushing, or immersing the tubular frame with a tissue precursor composition.

Clause 16: The method of any of clauses 10 to 15, wherein the applying the biomaterial scaffold comprises immersing the tubular frame in an annular mold comprising the tissue precursor composition.

Clause 17: The method of any of clauses 10 to 16, wherein the culturing comprises one or more of spraying, coating, brushing, or immersing the biomaterial scaffold with the culture medium.

Clause 18: The method of any of clauses 10 to 17, wherein the perforating comprises focusing an energy beam at predetermined locations along the tissue layer for predetermined periods of time.

Clause 19: The method of any of clauses 10 to 18, wherein the perforating comprises cutting the plurality of openings at predetermined locations along the tissue layer with a cutting tool.

Clause 20: The method of any of clauses 10 to 19, wherein the tissue layer comprises extracellular matrix.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Reference is made to the attached drawings, wherein elements having the same reference numeral designations represent similar elements throughout and wherein:

FIG. 3A is a schematic and conceptual illustration of an exploded view of assembly including an example tubular frame and an example annular mold.

FIG. 3B is a schematic and conceptual illustration of a top view of the tubular frame of FIG. 3A.

FIG. 3C is a schematic and conceptual illustration of the assembly of FIG. 3A in which the tubular frame is cultured in the annular mold.

FIG. 3D is a schematic and conceptual illustration of the assembly of FIG. 3C after culturing in which the tubular frame coated with a tissue layer is removed from the annular mold.

FIG. 3E is a schematic and conceptual illustration of a top view of the tubular frame of FIG. 3D coated with the tissue layer.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION OF THE DISCLOSURE

Implantable medical articles may reendothelialize after implantation to different extents. Medical articles, for example, stents, coated with extracellular matrix may reendothelialize more quickly that bare-metal stents, leading to lower restenosis rates. In some examples, a tissue-engineered stent may be formed by embedding a nitinol stent within a biomaterial scaffold containing biological cells, for example, fibroblasts and/or smooth muscle cells. The biomaterial scaffold may be transformed by the biological cells to tissue on culturing in a culture medium, for example, for a period of 2-4 weeks. After the conversion of the biomaterial to tissue is complete, the tissue-coated stent may be decellularized to remove substantially all biological cells or to leave substantially all biological cells dead or otherwise non-viable. In some examples, defects, for example, cuts, slits, openings, or windows, may be introduced in tissue-coated articles, allowing the tissue to contract and expand without being detached or separated from the articles. In some examples, the tissue may contract about struts of the stent due to cell-mediated forces and remodeling of tissue. In some examples, the tissue may contract or expand in response to mechanical forces exerted on the tissue.

Figure 1A:
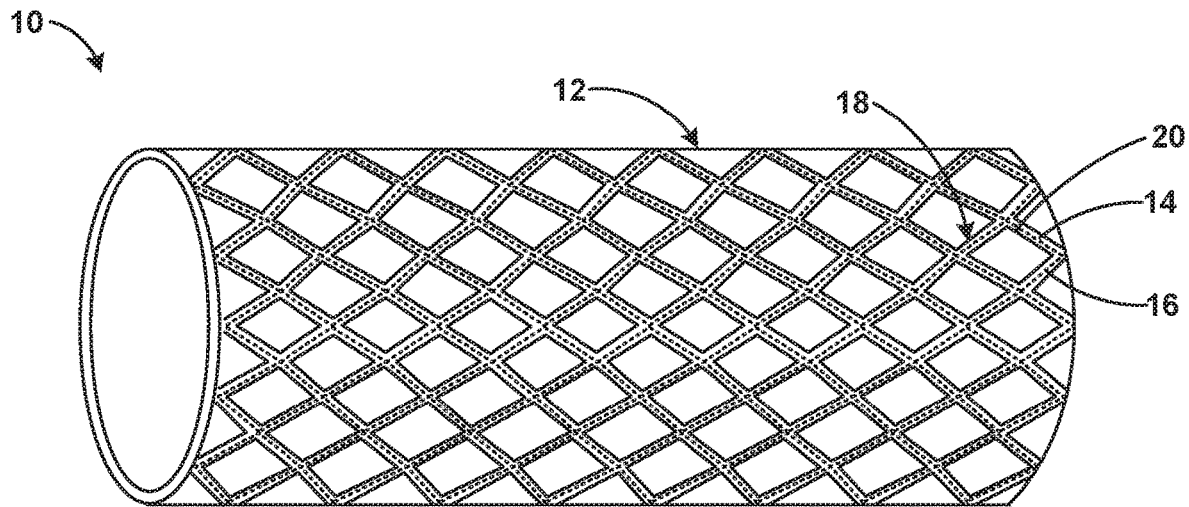
FIG. 1A is a schematic and conceptual illustration of an example article including a tubular frame including struts defining cells coated with a tissue layer defining defects.

FIG. 1A is a schematic and conceptual illustration of an example article 10 including a tubular frame 12 coated with a tissue layer 14. Tubular frame 12 may have a circular, oval, ellipsoidal, curved, undulating, polygonal, or any suitable predetermined cross-section. In some examples, tubular frame 12 defines an implantable medical device, for example, a stent, a shunt, or a tube. Tubular frame 12 extends along a longitudinal axis defined by respective ends of tubular frame 12. Tubular frame 12 includes struts 16 defining plurality of cells 18. Struts 16 may include any rigid or semi-rigid material capable of maintaining a predetermined structure. For example, struts 16 may include any suitable non-degradable or biodegradable material, for example, one or more of metal, alloy, polymer, or ceramic. Struts 16 of each cell of plurality of cells 18 may have substantially the same length and width, or may differ in one or both of length or width. In some examples, struts 16 may be porous, for example, including pores that admit biological cells, or a fluid. While tissue may form a coating or a layer, the coating or layer may be substantially integrated with, or inseparable from, tubular frame 12.

Each cell of plurality of cells 18 may include struts 16 arranged to maintain a predetermined shape or geometry of the respective cell in response to predetermined force or pressure applied on one or more regions of tubular frame 12. For example, each cell of plurality of cells 18 may include a closed polygon including at least three, or at least four, or more struts 16.

Figure 1B:
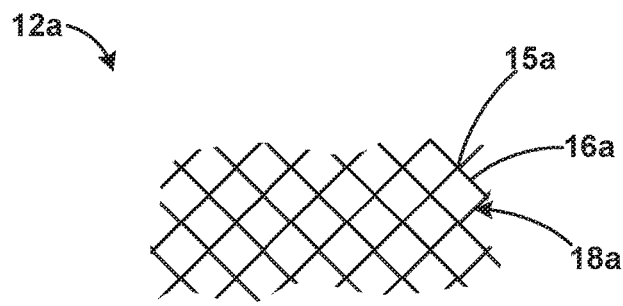
FIG. 1B is a schematic and conceptual illustration of a region of an example tubular frame including struts defining polygonal cells.

For example, FIG. 1B is a schematic and conceptual illustration of a region of an example tubular frame 12a including struts 16a defining polygonal plurality of cells 18a. Tubular frame 12a may be coated with a tissue layer (not shown in FIG. 1B), for example, as described with reference to FIG. 2A. In some examples, each cell of plurality of cells 18a may include struts 16a connected at respective apices 15a defining a polygon, for example, a rectangular polygon. In some examples, each cell of plurality of cells 18a may include undulating struts 16a connected at respective apices 15a. While cells 18a of FIG. 1B include four-sided polygons, in other examples, example articles according to the disclosure may include any suitable n-sided polygons, where n is a predetermined index. The polygons may be simple, or convex polygons, or other polygons, for example, as shown in FIG. 1C.

Figure 1C:
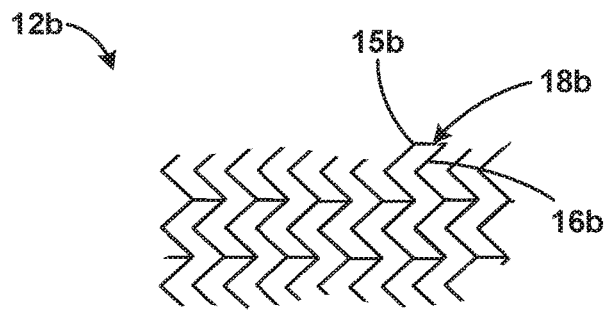
FIG. 1C is a schematic and conceptual illustration of a region of an example tubular frame including struts defining polygonal cells.

FIG. 1C is a schematic and conceptual illustration of a region of an example tubular frame 12b including struts 16b defining polygonal cells 18b. Struts 16b may be connected at apices 15b. Struts 16b may define a non-convex (or concave polygon), for example, as shown in FIG. 1C. Tubular frame 12b may be coated with a tissue layer (not shown in FIG. 1B), for example, a tissue layer defining a plurality of defects (not shown in FIG. 1B) according to the disclosure.

Turning back to FIG. 1A, tissue layer 14 may extend across substantially each cell of plurality of cells 18, for example, all but a few of plurality of cells 18. In some examples, tissue layer 14 extends across each cell of plurality of cells 18. In some examples, tissue layer 14 coats substantially all struts, for example, all but a few struts, of plurality of struts 16. In some examples, tissue layer 14 coats each strut of plurality of struts 16. Tissue layer 14 may include any suitable biological tissue, for example, tissue formed or generated by biological cells, or by a biological or biotechnological process. In some examples, tissue layer 14 may include a plurality of biological or live cells. In other examples, tissue layer 14 may be substantially decellularized, or substantially free of live cells. For example, cells may be present in tissue layer 14, but may be dead or otherwise non-viable cells. Decellularized tissue layer 14 may exhibit a reduced immune response or allergenicity compared to tissue layer 14 including cells. The tissue may be formed from a suitable precursor material. In some examples, tissue layer 14 includes extracellular matrix, or a variant, derivative, or analog of extracellular matrix. The extracellular matrix or analog may include one or more of collagen, fibronectin, laminin, glycosaminoglycans, or other components, for example, growth factors and cytokines. In some examples, the tissue may be formed by biological cells that convert the precursor material, for example, proteinaceous material including, but not limited to, fibrin, collagen, or alginate, or polymeric material including, but not limited to, PGA, PLA, or other biodegradable or biocompatible polymers. Tissue layer 14 may provide tubular frame 12 with a biocompatible surface. For example, tubular frame 12 including tissue layer 14 may reendothelialize more quickly compared to that of bare tubular frame 12 or tubular frame 12 otherwise without tissue layer 14.

In some examples, tissue layer 18 is discontinuous. For example, tissue layer 18 may define a plurality of defects 20, as shown in FIG. 1A. One or more defects of plurality of defects 20 may define a discontinuity, for example, a void, a gap, a window, an opening, a slit, or any predetermined discontinuity, in tissue layer 18. In some examples, substantially all cells, for example, all but a few cells, of plurality of cells 14 includes at least one defect of plurality of defects 20. In some examples, each cell of plurality of cells 14 includes a respective defect of plurality of defects 20. In some examples, one or more cells of plurality of cells 14 may include more than one defect of plurality of defects 20.

Plurality of defects 20 may allow one or more portions of tissue layer 14 to deform, for example, by sliding across or along a respective cell of plurality of cells 18a of tubular frame 12. The deformation of tissue layer 14 may allow tissue layer 14 to be retained on tubular frame 12 (for example, remain attached to or on tubular frame 12) even if tubular frame 12 changes shape or configuration. For example, a tissue layer that does not include defects may break or rupture in an uncontrolled manner, which may cause one or more portions of the tissue layer to separate from respective regions of tubular frame 12, leaving one or more cells of plurality of cells 18 without tissue layer, or leaving one or more struts of plurality of struts 16 without a coating of tissue layer. Such uncoated or uncovered portions of tubular frame 12 may expose bare material of plurality of struts 16 to a body lumen. In contrast, tissue layer 14 defining plurality of defects 20 may be substantially retained on plurality of struts 16a and on tubular frame 12 even when tubular frame 12 expands or contracts. For example, plurality of defects 20 may allow predetermined portions of tissue layer 14 to relax or deform within a predetermined tolerance in response to application of force or pressure on tubular frame 12, such that the force or pressure does not push, squeeze, or otherwise cause tissue layer 14 to be removed (for example, detached), from tubular frame 12. Thus, a bare material or exposed material of tubular frame 12 coated with tissue layer 14 that includes plurality of defects 20 may not be exposed to a body lumen in which tubular frame 12 is introduced, even in response to a force or pressure tending to change a configuration of tubular frame 12.

Thus, in some examples, plurality of cells 18 is configured to collapse to compress tubular frame 12 into a compressed state, where each defect of plurality of defects 20 is substantially closed in the compressed state. Instead, or in addition, plurality of cells 18 may be configured to expand to expand tubular frame 12 into an expanded state, where each defect of plurality of defects 20 is substantially open in the expanded state. In some examples, in the compressed state, tubular frame 12 may have an average diameter or cross-sectional dimension that is smaller than a corresponding average diameter or cross-sectional dimension in the expanded state. In some examples, in the compressed state, tubular frame 12 may have a length that is smaller than a corresponding length in the expanded state. In some examples, the compressed state of tubular frame may be associated with an undeployed configuration of tubular frame 12, for example, prior to implantation, or during transport to an implantation site. In some examples, the expanded state of tubular frame 12 may be associated with a deployed configuration of tubular frame 12, for example, when implanted at an implantation site.

While plurality of defects 20 may include one or more polygonal defects, for example, substantially rectangular defects, as shown in FIG. 1A, in other examples, plurality of defects 20 may include one or more defects having other shapes. For example, one or more defects of plurality of defects 20 may define at least one opening or at least one window in tissue layer 14, for example, an opening having a triangular, square, parallelepiped, rhomboidal, or n-sided polygonal shaped periphery, where n may be at least 3, or circular, ellipsoidal, curved, or any suitable closed opening. In some examples, the window may not be open, and may instead define a portion of tissue layer 14 that has a reduced thickness compared to other portions of tissue layer 14. In some examples, windows defining portions of reduced thickness may open in response to an applied force or pressure, generating respective openings in tissue layer 14. In some examples, one or more defects of plurality of defects 20 may define at least one slit that may open in response to applied forces or pressures. For example, the at least one slit or at least one opening may be configured to expand in response to an expansion of tubular frame 12 to define a respective window. For example, the at least one slit may expand along a direction transverse to a longitudinal axis or a major axis defined by the at least one slit. Instead of, or in addition to, transverse expansion, in some examples, the at least one slit may contract along a direction alone the longitudinal axis or the major axis defined by the at least one slit.

Plurality of defects 20 may include defects having substantially the same size or shape, or defects having different sizes or shapes. In some examples, substantially each cell of plurality of cells 18 defines the same or similar defects. In other examples, different groups of cells of plurality of cells 18 may define different defect geometries. Thus, respective defects of plurality of defects 20 may be distributed along respective cells of plurality of cells in any suitable predetermined pattern, for example, a pattern that allows portions of tissue layer 14 to deform in response to forces or pressures while substantially retaining tissue layer 14 on tubular frame 12. In some examples, one or more defects of plurality of defects 20 may change shape or size in response to deformations of tubular frame 12, for example, as described with reference to FIGS. 2A to 2F.

Figure 2F:
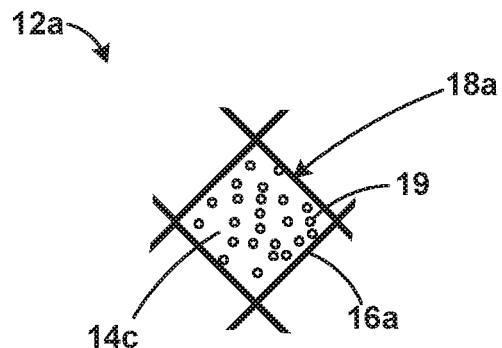
FIG. 2F is a schematic and conceptual illustration of a region of the example tubular frame of FIG. 1B including struts defining polygonal cells coated with a precursor tissue layer generated by biological cells.
Figure 2A:
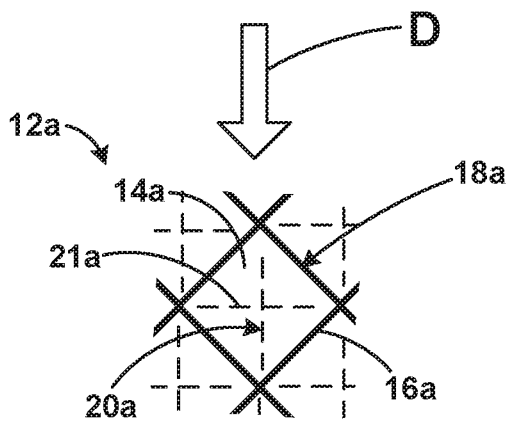
FIG. 2A is a schematic and conceptual illustration of a region of the example tubular frame of FIG. 1B, coated with a tissue layer defining a plurality of defects.

FIG. 2A is a schematic and conceptual illustration of a region of example tubular frame 12a of FIG. 1B, coated with tissue layer 14a defining plurality of defects 20a. Plurality of defects 20a includes at least one slit 21a, as shown in FIG. 2A. The slit may be defined by edges of tissue layer 14a substantially in contact with each other, for example, a closed slit, or edges of tissue layer 14a having a predetermined separation respect to each other, for example, a separation of at least 0.01 millimeter (mm), or at least 0.1 mm, or at least 1 mm, for example, an open slit. The at least one slit may deform to define an opening in response to an applied force or pressure, for example, deforming from slits to openings, as described with reference to FIGS. 2B to 2E. In some examples, the at least one slit of plurality of defects 20a may only temporary deform into an opening in response to a first force or pressure on tubular frame 12a, for example, by movement of flaps adjacent the at least one slit, and be restored to its initial slit form, in response to a second force or pressure on tubular frame 12a.

Figure 2B:
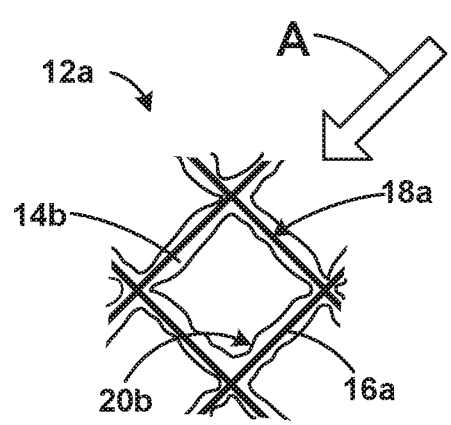
FIG. 2B is a schematic and conceptual illustration of a region of the example tubular frame of FIG. 2A in which at least one defect of the plurality of defects is opened into a ragged window.

FIG. 2B is a schematic and conceptual illustration of a region of example tubular frame 12a of FIG. 2A in which at least one defect of plurality of defects 20a is opened into a ragged window 20b. FIG. 2C is a schematic and conceptual illustration of a cross-section of example strut 16a of example tubular frame 12a of FIG. 2B having a ragged tissue coating, formed by a tissue layer 14b. In some examples, in response to a force or pressure applied through tubular frame 12a or otherwise on tissue layer 14a, tissue layer 14a may deform into tissue layer 14b (as represented by arrow A) defining a different shape than tissue layer 14a, for example as shown in FIGS. 2B and 2C. For example, ragged window 20b may be defined by adjacent portions of tissue layer 14b deformed by movement of corresponding flaps or portions of tissue layer 14a in response to the force or pressure. For example, material of tissue layer 14a may flow, migrate, or otherwise transport in vicinity of respective defects of plurality of defects 20a to eventually form tissue layer 14b defining ragged window 20b. Ragged window 20b may eventually transform to a smooth window, for example, as described with reference to FIG. 2D.

Figure 2D:
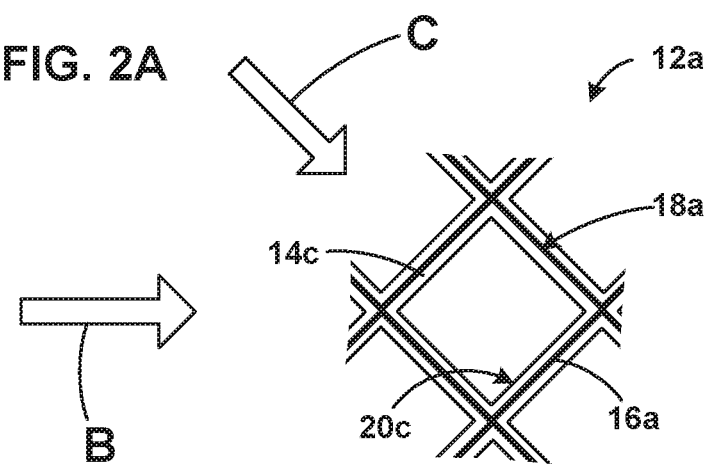
FIG. 2D is a schematic and conceptual illustration of a region of the example tubular frame of FIG. 2A in which at least one defect of the plurality of defects is opened into a smooth window.
Figure 2C:
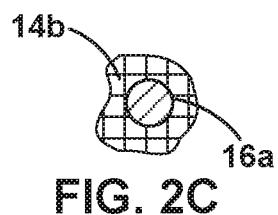
FIG. 2C is a schematic and conceptual illustration of a cross-section of an example strut of the example tubular frame of FIG. 2B having a ragged tissue coating formed by a tissue layer.
Figure 2E:
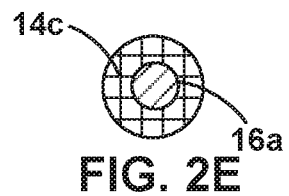
FIG. 2E is a schematic and conceptual illustration of a cross-section of an example strut of the example tubular frame of FIG. 2D having a smooth tissue coating formed by a tissue layer.

FIG. 2D is a schematic and conceptual illustration of a region of example tubular frame 12a of FIG. 2A in which at least one defect of plurality of defects 20a is opened into a smooth window 20c. FIG. 2E is a schematic and conceptual illustration of a cross-section of example strut 16a of example tubular frame 12 of FIG. 2D, having a smooth tissue coating formed by a tissue layer 14c. In some examples, in response to a force or pressure applied through tubular frame 12a or otherwise on tissue layer 14b, tissue layer 14b may eventually deform into tissue layer 14c (as represented by arrow B) defining a different shape than tissue layer 14a or 14b, for example as shown in FIGS. 2D and 2E. For example, ragged window 20b may transform into smooth window 20c by movement of corresponding flaps or portions of tissue layer 14b in response to the force or pressure. For example, material of tissue layer 14b may flow, migrate, or otherwise transport in vicinity of ragged window 20b to eventually form tissue layer 14c defining smooth window 20c. In some examples, tissue layer 14a defining at least one slit in plurality of defects 20a may deform into tissue layer 14c (as represented by arrow C) defining at least one smooth window 20c, as represented by the arrow between FIGS. 2A and 2D, for example, by flow, migration, or transport of material in vicinity of plurality of defects 20a to eventually form smooth window 20c. While tissue layer 14c may define a smooth tissue coating having a substantially circular cross-section about strut 16a, as shown in FIG. 2E, in other examples, the cross-section may be ellipsoidal, polygonal, polygonal with curved corners, or any other closed cross-section.

Thus, in some examples, at least one defect of plurality of defects 20a may define a respective window in each cell of plurality of cells 18a. In some examples, each respective window may define a polygonal edge. In some examples, each respective window may define a curved edge.

While the configurations of tissue layers 14b and 14c described with reference to FIG. 2C to 2E may be formed from tissue layer 14a described with reference to FIG. 2A, one or more of tissue layers 14a, 14b, or 14c may be formed from a precursor tissue layer, as described with reference to FIG. 2F.

FIG. 2F is a schematic and conceptual illustration of a region of example tubular frame 12a of FIG. 1B including struts 16a defining polygonal cells 18a coated with a precursor tissue layer 14c generated by biological cells 19. As shown in FIG. 2F, precursor tissue layer 14c may define substantially none or no defects. Defects may be introduced into precursor tissue layer 14c, for example, by cutting with an energy beam or a mechanical cutter, as described herein, to define at least one slit, or at least one window or opening. For example, at least one slit may be cut into tissue layer 14c at respective cells of plurality of cells 18a to define respective defects of plurality of defects 20a, as shown in FIG. 2A, or to define ragged windows 20b, as shown in FIG. 2B, or to define smooth windows, as shown in FIG. 2C. Thus, in some examples, ragged or smooth windows 20b or 20c of FIG. 2B or 2C may be directly formed from precursor tissue layer 14c. Similarly, plurality of defects 20a may be introduced into precursor tissue layer 14c to form tissue layer 14a of FIG. 2A (as represented by arrow D).

Biological cells 19 may include any suitable living cells capable of forming precursor tissue layer 14c. Biological cells 19 may include, for example, one or both of human or animal fibroblasts, smooth muscle cells, endothelial cells, epithelial cells, or cells derived from stem cells. Biological cells 19 may be derived from a patient, from an animal, or from another source, for example, genetically modified or engineered cells. In some examples, biological cells 19 may include one or more of fibroblasts, smooth muscle cells, endothelial cells, epithelial cells, mesenchymal stem cells, bone marrow-derived stem cells, adipose-derived stem cells, hair follicle-derived stem cells, autologous amniotic fluid cells, pluripotent stem cells, pluripotent stem cell-derived progenitor cells, or cells derived from one or more of these cells. In some examples, biological cells 19 may form precursor tissue layer 14c from a biomaterial scaffold, as described herein. After biological cells 19 form precursor tissue layer 14c, they may be preserved in precursor tissue layer 14c and in tissue layers formed from precursor tissue layer 14c, for example, tissue layers 14a,14b, or 14c (not shown in FIGS. 2A, 2B, and 2C). In other examples, precursor tissue layer 14c may be decellularized to substantially remove biological cells 19, as described herein. Decellularization may form precursor tissue layer 14c and tissue layers formed from precursor tissue layer 14c, for example, tissue layers 14a, 14b, or 14c, substantially free of biological cells, as shown in FIGS. 2A to 2E.

While the example articles of FIGS. 2A to 2F are described with reference to tubular frame 12a of FIG. 1B, example articles according to the disclosure may include any suitable tubular frame according to the disclosure, for example, tubular frame 12 of FIG. 1A, tubular frame 12b of FIG. 1C. Thus, tissue layers 14, 14a, 14b, or 14c, or other tissue layers according to the disclosure may be formed on tubular frames 12, 12a, 12b, or any other suitable tubular frames.

Example articles according to the disclosure may be formed using any suitable systems, assemblies, and techniques, for example, example assemblies and systems described with reference to FIGS. 3A to 3E and example techniques described with reference to FIG. 4.

FIG. 3A is a schematic and conceptual illustration of an exploded view of an assembly 30 including example tubular frame 12 and an example annular mold 34. Tubular frame 12 may have a structure and composition that is the same as or similar to tubular frames 12, 12a, or 12b, or may include any suitable tubular frame including a plurality of struts. In some examples, tubular frame 12 may include a sidewall defining a plurality of rigid or semi-rigid connecting elements such as lines, rods, beams, braces, strips, or sections, or other connecting elements, and corresponding openings defined by the connecting elements. FIG. 3B is a schematic and conceptual illustration of a top view of tubular frame 12 of FIG. 3A. Tubular frame 12 may have a substantially circular cross-section, as shown in FIG. 3A. However, in other examples, tubular frame 12 may have an ellipsoidal, curved, undulating, polygonal, or any suitable predetermined cross-section.

Bare tubular frame 12 may initially not have any tissue layer, as shown in FIGS. 3A and 3B. A tissue layer may be formed on tubular frame 12 from a biomaterial scaffold 36 applied to or in contact with tubular frame 12. Biomaterial scaffold 36 may include a tissue precursor that may be converted to a tissue layer, for example, by live or viable biological cells. The biological cells may include natural cells or genetically modified or engineered cells. In some examples, biomaterial scaffold 36 may include one or more of natural or synthetic proteins or biocompatible polymers. Proteins may include fibrin, collagen, alginate, or any suitable protein. Biocompatible polymers may include polyglycolic acid, polylactic acid, or any suitable biocompatible, bioconvertible, or biodegradable polymer. In some examples, biomaterial scaffold 36 includes one or more of fibrin, collagen, alginate, chitin, gelatin, polyglycolic acid, or polylactic acid. In some examples, biomaterial scaffold 36 may include hydrolytically degradable polymers, poly (α-esters), polyglycolide, polylactides, poly(lactide-co-glycolide), polydioxanone, polycaprolactone, poly(trimethylene carbonate) bacterial polyesters, polyurethanes, poly(ester amide), poly(ortho esters), polyanhydrides, poly (anhydride-co-imide), cross-linked polyanhydrides, poly (propylene fumarate), pseudo poly(amino acid), poly(alkyl cyanoacrylates), polyphosphazenes, polyphosphoester, enzymatically degradable polymers, proteins and poly (amino acids), collagen, elastin, elastin-like peptides, albumin, fibrin, or polysaccharides, or any suitable biodegradable polymers described in the article titled "Biodegradable polymers as biomaterials" (Progress in Polymer Science, 32 (2007) 762-798) by Nair et al., incorporated herein in its entirety by reference. Biomaterial scaffold 36 may include a liquid, gel, emulsion, colloid, semi-solid, or solid composition. In some examples, the state of biomaterial scaffold 36 may change from one of liquid, gel, emulsion, colloid, semi-solid, or solid to another of liquid, gel, emulsion, colloid, semi-solid, or solid in response to predetermined changes in temperature, pH, cellular activity, or other predetermined conditions before, during, or after applying biological scaffold 36 to tubular frame 12. In some examples, annular mold 34 may contain tissue precursor 36, and tubular frame may be introduced into biomaterial scaffold 36 in annular mold 34, as described with reference to FIG. 3C.

FIG. 3C is a schematic and conceptual illustration of an assembly 30a (similar to assembly 30 of FIG. 3A) in which tubular frame 12 is cultured in annular mold 34. Tubular frame 12 is introduced into annular mold 34 to be in contact with biomaterial scaffold 36. Biomaterial scaffold 36 may be introduced into a culture media 38. Culture media 38 may include a liquid or gel composition configured to promote conversion of biomaterial scaffold 36 to a tissue layer, for example, by viable or live cells, such as biological cells 19 (not shown in FIGS. 3A to 3E). For example, biological cells may be seeded in either biomaterial scaffold 36 or in culture media 38. Culture media 38 may include nutrients predetermined to promote activity of predetermined biological cells. Biomaterial scaffold 36 may be maintained in culture media 38 under predetermined conditions, for example, temperature, pH, nutrient composition, and time, so that biological cells may eventually convert at least a portion of biomaterial scaffold 36 to form a tissue layer. After the culturing, tubular frame 30 may be removed from annular mold 34, as described with reference to FIG. 3D.

FIG. 3D is a schematic and conceptual illustration of an assembly 30b (similar to assembly 30a of FIG. 3C) after culturing in which tubular frame 12 coated with tissue layer 14 is removed from annular mold 34. FIG. 3E is a schematic and conceptual illustration of a top view of the tubular frame of FIG. 3D coated with the tissue layer. Tissue layer 14 may be the same as or similar to precursor tissue layer 14c described with reference to FIG. 2F, or any other tissue layer according to the disclosure. In some examples, tissue layer 14 may initially be substantially continuous, and may be cut using cutting tool 40 to generate a plurality of defects in tissue layer 14, for example, any suitable plurality of defects as described in the disclosure. Cutting tool 40 may include a mechanical cutting element, for example, a blade, a punch, or a die, or an energy beam, for example, laser or e-beam, capable of cutting predetermined regions of tissue layer 14 to form a plurality of defects. In some examples, cutting tool 40 may define a major surface defining a plurality of embossing or cutting features, and the major surface of cutting tool 40 may be pressed onto corresponding regions of tissue layer 14 on tubular frame 12, for example, by moving or rolling cutting tool 40 about or around tubular frame 14, to punch, emboss, or cut tissue layer 14 with the embossing or cutting features, to define the plurality of defects in tissue layer 14.

Thus, example assemblies and systems according to the disclosure may be used to form example articles including example tissue layers defining a plurality of defects on example tubular frames.

Figure 4:
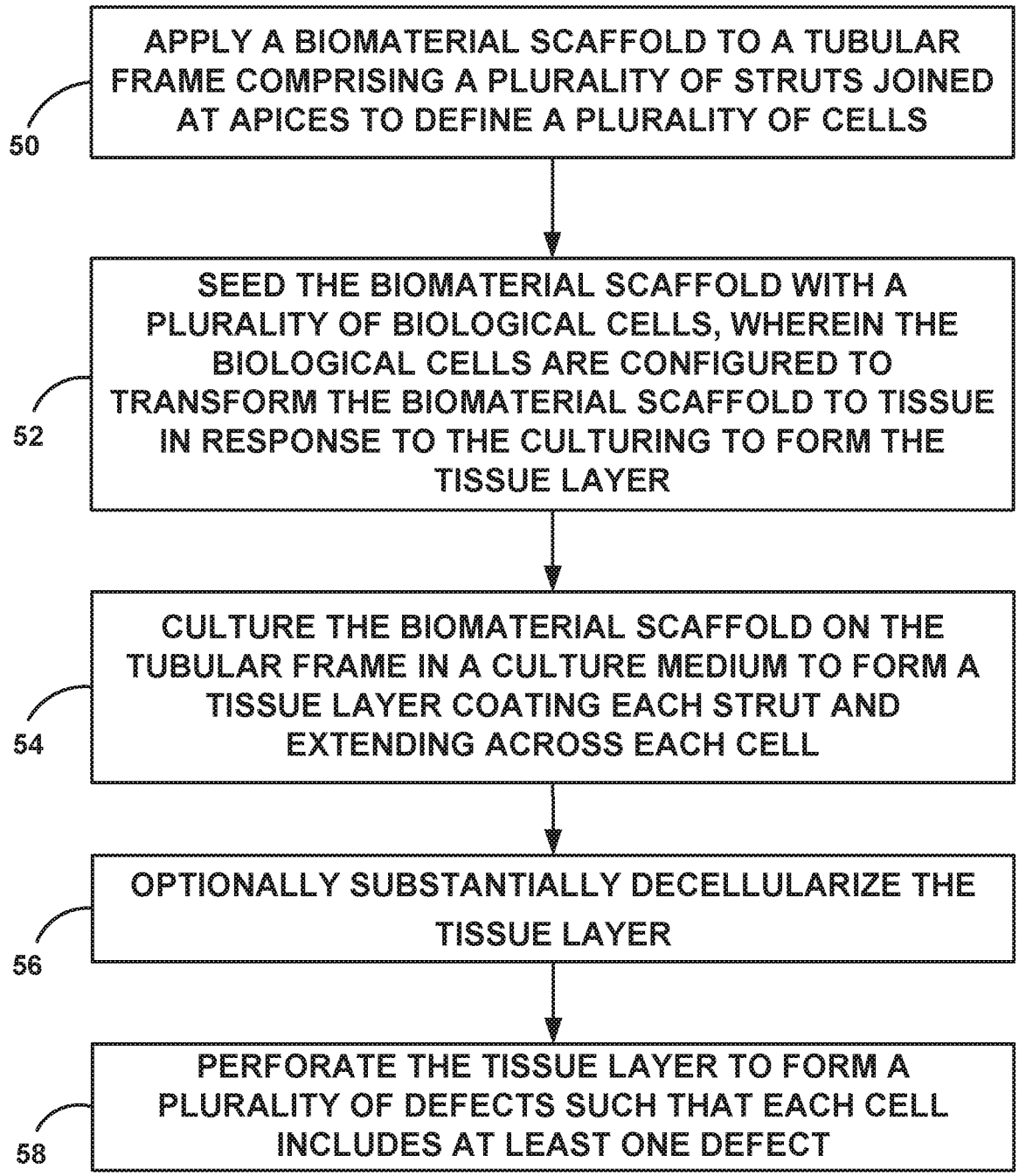
FIG. 4 is a flowchart illustrating an example technique for forming an example tissue-coated tubular frame.

FIG. 4 is a flowchart illustrating an example technique for forming an example tissue-coated tubular frame. The example technique of FIG. 4 is described with reference to example articles of FIGS. 1A to 1C and 2A to 2F, and with reference to example assemblies and systems of FIGS. 3A to 3E, for conciseness and convenience. However, the example technique of FIG. 4 may be implemented using any suitable assemblies or systems to form any suitable example articles according to the disclosure.

In some examples, the example technique of FIG. 4 includes applying biomaterial scaffold 36 to tubular frame 12 including plurality of struts 16 joined at apices 15 to define plurality of cells 18 (50). In some examples, biomaterial scaffold 36 includes one or more of fibrin, collagen, alginate, polyglycolic acid, or polylactic acid. Applying biomaterial scaffold 36 may include one or more of spraying, coating, brushing, or immersing tubular frame 12 with a tissue precursor composition. In some examples, applying biomaterial scaffold 36 (50) includes immersing tubular frame 12 in annular mold 34 including the tissue precursor composition.

The tissue precursor composition may be biomaterial scaffold 36 itself, or may be a different composition that is transformed into biomaterial scaffold 36, for example, by chemical or thermodynamic processes, for example, change in physical or chemical state. While tubular frame 12 may be immersed in biomaterial scaffold 36 in annular mold 34, as described with reference to FIGS. 3A to 3E, in other examples, biomaterial scaffold 36 may be contained in any suitable container, and tubular frame 12 may be introduced or immersed in biomaterial scaffold 36. In some examples, no container may be used, and biomaterial scaffold 36 may be directly applied to tubular frame 12 by an applicator, for example, a brush, a spray, or a coater.

In some examples, the example technique includes, before culturing biomaterial scaffold 36, seeding biomaterial scaffold 36 with plurality of biological cells 19 (52). Biological cells are configured to transform biomaterial scaffold 36 to tissue (for example, biological tissue in response to the culturing to form tissue layer 14. The transformation of biomaterial scaffold 36 to tissue layer 14 may include one or more of chemical cross-linking, formation and alteration of chemical bonds, or biological changes to a composition of biomaterial scaffold 36, for example, by action of biological cells 19. Biological cells 19 may include, for example, one or both of fibroblasts or smooth muscle cells.

The example technique includes culturing biomaterial scaffold 36 on tubular frame 12 in culture medium 38 to form tissue layer 14 coating each strut of plurality of struts 16 and extending across each cell of plurality of cells 18 (54). In some examples, instead of, or in addition to, seeding biomaterial scaffold 36 with biological cells 19, biological cells 19 may be introduced in culture medium 38, for example, during or before the culturing 54. In some examples, the culturing (54) includes one or more of spraying, coating, brushing, or immersing biomaterial scaffold 36 with culture medium 38. The culturing (54) may be performed in a batch process or in a static volume of culture medium, or in a continuous process or a flowing volume of culture medium 38, for example, in a bioreactor.

In some examples, the example technique further includes, after the culturing (54), substantially decellularizing tissue layer 14 (56). The decellularizing (56) may include any suitable treatment that may one or more of reduce or prevent the growth or activity of biological cells 19, kill biological cells 19, or remove biological cells 19 from tissue layer 14, for example, trypsin-EDTA treatment, washing with detergent, washing with EDTA solution, freezing, dehydration, depressurizing, vacuum, radiation, or lyophilization. In some examples, after the decellularizing (56), less than 50%, or less than 75%, or less than 90%, or less than 95% of an initial population of biological cells 19 may remain viable, or may remain physically within tissue layer 14.

The example technique may include perforating tissue layer 14 to form plurality of defects 20 such that each cell of plurality of cells 18 includes at least one defect of plurality of defects 20 (58). In examples in which the example technique includes both the decellularizing (56) and the perforating (58), the perforating (58) may be performed before or after the decellularizing (56). In some examples, the perforating (58) includes focusing an energy beam, for example, from a laser source or an e-beam source, at predetermined locations along tissue layer 14 for predetermined periods of time. In some examples, the perforating (58) includes cutting a plurality of openings at predetermined locations along tissue layer 14 with cutting tool 40.

Various examples have been described. These and other examples are within the scope of the following claims.

What is claimed is:

1. An article comprising:
   a tubular frame extending along a longitudinal axis, the tubular frame comprising:
      a plurality of struts joined at apices to define a plurality of cells, each cell of the plurality of cells comprising a group of struts of the plurality of struts; and
      a tissue layer coating each strut of the plurality of struts and being substantially integrated with the plurality of struts, wherein the tissue layer extends across each cell of the plurality of cells, the tissue layer defining a plurality of defects, each cell of the plurality of cells including a respective defect of the plurality of defects, and wherein the tissue layer contacts each strut of the plurality of struts along an entire outer perimeter of each strut.

2. The article of claim 1, wherein at least one defect of the plurality of defects includes at least one slit or at least one opening.

3. The article of claim 2, wherein the at least one slit or at least one opening is configured to expand in response to an expansion of the tubular frame to define a respective window.

4. The article of claim 1, wherein at least one defect of the plurality of defects defines a respective window in each cell of the plurality of cells.

5. The article of claim 4, wherein each respective window defines a polygonal edge.

6. The article of claim 4, wherein each respective window defines a curved edge.

7. The article of claim 1, wherein the plurality of cells is configured to:
   collapse to compress the tubular frame into a compressed state, wherein each defect of the plurality of defects is substantially closed in the compressed state; and
   expand to expand the tubular frame into an expanded state, wherein each defect of the plurality of defects is substantially open in the expanded state.

8. The article of claim 1, wherein the tissue layer is substantially free of live cells.

9. The article of claim 1, wherein the tissue layer comprises extracellular matrix.

10. The article of claim 1, wherein the tissue layer coating each strut of the plurality of struts includes a first portion of the tissue layer that contact the plurality of struts and a second portion of the tissue layer that extends across each cell of the plurality of cells, and wherein the first portion of the tissue layer in contact with the plurality of struts remains fixed in place in response to an expansion of the tubular frame.

11. The article of claim 1, wherein the tissue layer is configured such that, in response to an expansion of the tubular frame, the plurality of defects form respective openings in the tissue layer that are substantially aligned with and have substantially the same shape as corresponding openings between the plurality of struts.

12. An article comprising:
a tubular frame extending along a longitudinal axis, the tubular frame comprising:
a plurality of struts joined at apices to define a plurality of cells, each cell of the plurality of cells comprising a group of struts of the plurality of struts; and
a tissue layer coating each strut of the plurality of struts such that a first portion of the tissue layer contacts the plurality of struts and a second portion of the tissue layer extends across each cell of the plurality of cells, the tissue layer defining a plurality of defects, each cell of the plurality of cells including a respective defect of the plurality of defects, wherein the first portion of the tissue layer in contact with the plurality of struts remains fixed in place in response to an expansion of the tubular frame.

13. The article of claim 12, wherein at least one defect of the plurality of defects includes at least one slit or at least one opening.

14. The article of claim 13, wherein the at least one slit or at least one opening is configured to expand in response to the expansion of the tubular frame to define a respective window.

15. The article of claim 12, wherein the tissue layer contacts each strut of the plurality of struts along an entire outer perimeter of each strut.

16. The article of claim 12, wherein the tissue layer is configured such that, in response to the expansion of the tubular frame, the plurality of defects form respective openings in the tissue layer that are substantially aligned with and have substantially the same shape as corresponding openings between the plurality of struts.

* * * * *